United States Patent [19]

Abatjoglou et al.

[11] Patent Number: 4,522,933

[45] Date of Patent: Jun. 11, 1985

[54] HYDROFORMYLATION CATALYST CONTAINING BISPHOSPHINE MONOOXIDE LIGANDS

[75] Inventors: Anthony G. Abatjoglou; Ernst Billig, both of Charleston, W. Va.

[73] Assignee: Union Carbide Corporation, Danbury, Conn.

[21] Appl. No.: 476,314

[22] Filed: Mar. 17, 1983

Related U.S. Application Data

[62] Division of Ser. No. 293,190, Aug. 17, 1981, Pat. No. 4,400,548.

[51] Int. Cl.$^3$ .............................................. B01J 31/24
[52] U.S. Cl. ..................................... 502/161; 502/166; 556/18
[58] Field of Search .................... 252/431 P; 502/161, 502/166

[56]  References Cited

U.S. PATENT DOCUMENTS

| | | | |
|---|---|---|---|
| 3,426,021 | 2/1969 | Seyferth | 260/246 |
| 3,527,809 | 9/1970 | Pruett et al. | 260/604 |
| 3,560,572 | 2/1971 | Deffiner | 568/454 |
| 3,859,359 | 1/1975 | Keblys | 568/454 |
| 4,139,565 | 2/1979 | Unruh et al. | 260/604 HF |
| 4,148,830 | 4/1979 | Pruett et al. | 260/604 HF |
| 4,152,344 | 5/1979 | Unruh | 260/439 CY |
| 4,169,861 | 10/1979 | Hughes | 568/454 |
| 4,197,253 | 4/1980 | Kaplan | 252/431 P X |
| 4,215,077 | 7/1980 | Matsumoto et al. | 568/454 |
| 4,230,641 | 10/1980 | Bartish | 568/454 |
| 4,247,486 | 1/1981 | Brewester et al. | 568/454 |
| 4,260,828 | 4/1981 | Morrell et al. | 568/454 |
| 4,283,562 | 8/1981 | Billig et al. | 568/454 |
| 4,298,541 | 11/1981 | Oswald et al. | 568/454 |
| 4,302,401 | 11/1981 | Oswald | 568/454 |

FOREIGN PATENT DOCUMENTS

| | | |
|---|---|---|
| 1812504 | 12/1973 | Fed. Rep. of Germany . |
| 2922757 | 6/1979 | Fed. Rep. of Germany . |
| 3030108 | 4/1981 | Fed. Rep. of Germany . |
| WO80/01689 | 8/1980 | PCT Int'l Appl. . |
| WO80/01690 | 8/1980 | PCT Int'l Appl. . |
| WO80/01691 | 8/1980 | PCT Int'l Appl. . |
| WO80/01692 | 8/1980 | PCT Int'l Appl. . |
| 2014138 | 8/1979 | United Kingdom . |

OTHER PUBLICATIONS

"J. of Molecular Catalysis" vol. 3, pp. 221-226 (1977/1978), by A. R. Sanger.
"Platinum Metals Review" vol. 24, pp. 95 to 99 (1980), T. B. Rauchfuss.
"Inorganic Chemistry" vol. 14, pp. 656 to 660 #3 (1975), by S. O. Grim et al.

*Primary Examiner*—Patrick P. Garvin
*Attorney, Agent, or Firm*—Reynold J. Finnegan

[57]  ABSTRACT

A hydroformylation process for producing aldehydes using a bisphosphine monooxide ligand and catalytic precursor solutions for said process.

7 Claims, No Drawings

HYDROFORMYLATION CATALYST CONTAINING BISPHOSPHINE MONOOXIDE LIGANDS

This application is a division of our prior U.S. application Ser. No. 293,190, filed Aug. 17, 1981, now U.S. Pat. No. 4,400,548.

FIELD OF THE INVENTION

This invention relates to an improved process for preparing aldehydes by the hydroformylation of an olefinically unsaturated organic compound in the presence of a rhodium-phosphorus complex catalyst and free phosphorus ligand, the improvement comprising employing as the catalyst for said process a rhodium-bisphosphine monooxide complex catalyst and as the free phosphorus ligand for said process an organic tertiary bisphosphine monooxide ligand.

BACKGROUND OF THE INVENTION

Processes for forming an aldehyde by the hydroformylation of an olefinically unsaturated organic compound in the presence of a rhodium phosphorus complex catalyst and free phosphorus ligand are well known in the art, as seen, by U.S. Pat. Nos. 3,527,809; 4,148,830; and 4,247,486. The most commonly recommended phosphorus ligands are monophosphines and monophosphite compounds, especially triphenylphosphine.

For instance, U.S. Pat. No. 3,527,809, the entire disclosure of which is incorporated herein by reference thereto, discloses a hydroformylation process where olefinically unsaturated organic compounds are hydroformylated with carbon monooxide and hydrogen in the presence of a rhodium-phosphorus complex catalyst and free phosphorus ligand to produce aldehydes in high yields at low temperatures and pressures, where the normal to iso- (or branch chain) aldehyde isomer ratio of product aldehydes is high.

It is also known that, under hydroformylation conditions, some of the product aldehydes may condense to form high boiling aldehyde condensation by-products such as aldehyde dimers or trimers. Commonly-assigned U.S. Pat. No. 4,148,830, the entire disclosure of which is incorporated herein by reference thereto, discloses the use of these high boiling liquid aldehyde consensation by-products as a reaction solvent for the catalyst.

In addition, commonly-assigned U.S. Pat. No. 4,247,486, the entire disclosure of which is incorporated herein by reference thereto, discloses a liquid phase hydroformylation reaction using a rhodium-phosphorus complex catalyst, wherein the aldehyde reaction products and some of their higher boiling condensation products are removed in vapor form from the catalyst containing liquid body (or solution) at the reaction temperature and pressure. The aldehyde reaction products and the condensation products are condensed out of the off gas from the reaction vessel in a product recovery zone and the unreacted starting materials (e.g., carbon monooxide, hydrogen and/or alpha-olefin) in the vapor phase from the product recovery zone are recycled to the reaction zone. Furthermore, by recycling gas from the product recovery zone coupled with make-up starting materials to the reaction zone in sufficient amounts, it is possible, using a $C_2$ to $C_5$ olefin as the alpha-olefin starting material, to achieve a mass balance in the liquid body in the reactor and thereby remove from the reaction zone at a rate at least as great as their rate of formation essentially all the higher boiling condensation products resulting from self condensation of the aldehyde product.

It is also known in the prior art that even in the absence of intrinsic poisons there may be deactivation of rhodium-phosphorus hydroformylation catalysts under hydroformylation conditions. Commonly-assigned U.S. Pat. No. 4,277,627, the entire disclosure of which is incorporated herein by reference thereto, indicates that the deactivation of rhodium hydroformylation catalysts under hydroformylation conditions in the substantial absence of extrinsic poisons is due to the combination of the effects of temperature, phosphine ligand: rhodium mole ratio, and the partial pressures of hydrogen and carbon monoxide and is termed an intrinsic deactivation. It is further disclosed therein that this intrinsic deactivation can be reduced or substantially prevented by establishing and controlling and correlating the hydroformylation reaction conditions to a low temperature, low carbon monoxide partial pressure and high free triarylphosphine ligand: catalytically active rhodium mole ratio.

Thus, despite the obvious advantages of the above inventions, the discovery that the use of rhodium catalysts which may prove to be more robust than conventional rhodium-based catalysts in that they may be able to better withstand more severe reaction conditions and/or improve the economics of the hydroformylation process is of no small importance to the state of the art.

SUMMARY OF THE INVENTION

It has now been discovered that organic tertiary bisphosphine monooxide ligands can be employed as the phosphorus ligand in the rhodium catalyzed hydroformylation of a wide variety of olefinically unsaturated organic starting materials to provide numerous advantages relative to heretofore commonly employed monophosphine ligands. For example, in the hydroformylation of alpha-olefins desirably very high linear to branched aldehyde selectivities are generally obtainable with lower ligand concentrations. In addition, certain bisphosphine monooxide ligands have even been found to provide a higher linear to branched aldehyde selectivity. Another advantage of the use of the bisphosphine monooxide ligands is the significantly improved high temperature catalyst stability observed. Yet another advantage of the use of bisphosphine monooxide ligands is lower rate of isomerization of alpha-olefins to internal olefins that has been found to occur during hydroformylation. A still further advantage of the use of the bisphosphine monooxide ligands is an observed decrease in hydrogenation, i.e., that side reaction of the alpha-olefin to its corresponding alkane compound that can occur during hydroformylation. The use of the bisphosphine monooxide ligands have also been found to provide better catalyst stability in the hydroformylation of functional olefins such as allyl alcohol and alpha, omega dienes as well as provide higher linear aldehyde process efficiencies in the hydroformylation of said functional olefins by also reducing such like side reactions as isomerization and hydrogenation of the starting functional olefin.

Thus, it is an object of this invention to provide an improved rhodium complex catalyst hydroformylation process for producing aldehydes wherein the phosphorus ligand of the rhodium-complex catalyst as well as the free phosphorus ligand present in said process is an organic tertiary bisphosphine monooxide. It is also an object of this invention to provide rhodium-bisphosphine monooxide complex catalytic precursor solutions suitable for use in said hydroformylation process. Other objects and advantages of this invention will become readily apparent from the following written description and appended claims.

Accordingly, a generic aspect of this invention can be described as an improved process for producing aldehydes by the hydroformylation of an olefinically unsaturated organic compound with carbon monoxide and hydrogen in the presence of a rhodium-phosphorus ligand complex catalyst and free phosphorus ligand, the improvement comprising employing as the phosphorus ligand of said complex catalyst and as the free phosphorus ligand in said process an organic tertiary bisphosphine monooxide ligand having the general formula:

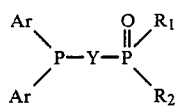

wherein each Ar group represents an identical or different substituted or unsubstituted aryl radical, each $R_1$ and $R_2$ group represents an identical or different substituted or unsubstituted monovalent hydrocarbon radical and Y represents a divalent bridging group.

Another generic aspect of this invention comprises rhodium-bisphosphine monooxide complex catalyst precursor solutions suitable for use in said hydroformylation processes.

DESCRIPTION OF THE PREFERRED EMBODIMENTS

Basically the hydroformylation process of this invention comprises the reaction of an olefinically unsaturated compound, carbon monoxide and hydrogen in the presence of a rhodium-bisphosphine monooxide complex catalyst and free bisphosphine monooxide ligand to produce saturated aldehydes. Such processes for forming aldehydes by the hydroformylation reaction (oxo synthesis) employing known rhodium-phosphorus complex catalysts and free phosphorus ligand are well known in the art as seen, for example, by U.S. Pat. Nos. 3,527,809, 4,148,830 and 4,247,486. Accordingly, the reaction conditions and processing techniques of this invention may correspond to any of the known reaction conditions and processing techniques heretofore employed in conventional hydroformylation reactions designed to produce aldehydes, since such conditions are not critical to this invention.

For instance, the hydroformylation process can be conducted in continuous, semi-continuous, or batch fashion and involve a liquid recycle or a gas recycle operation as desired. Likewise, the manner or order of addition of the reaction ingredients, catalyst and solvent are also not critical and may be accomplished in any conventional fashion.

In general, the hydroformylation reaction is preferably carried out in a liquid reaction medium that contains a solvent for the catalyst preferably one in which both the olefinically unsaturated compound and catalyst are substantially soluble, and free organic tertiary bisphosphine monooxide ligand.

Thus, as is the case with prior art hydroformylation processes that employ a rhodium-phosphorus complex catalyst and free phosphorus ligand, it is essential that the process of this invention be effected in the presence of free organic tertiary bisphosphine monooxide ligand. By "free ligand" is meant organic tertiary bisphosphine monooxide that is not tied (bound) to or complexed with the rhodium atom in the active rhodium-bisphosphine monooxide catalyst.

The reaction conditions for effecting the hydroformylation process of this invention can be those heretofore conventionally used and may comprise a reaction temperature of from about 45° C. to about 200° C. and pressures of from about 1 to 10,000 psia. However, the preferred hydroformylation process of this invention will be that process which is most efficient in producing normal aldehyde isomer product, i.e., straight chained aldehyde as distinguished from its isomeric or branched chain aldehyde product. The optimization of the reaction conditions necessary to achieve the best results and efficiency desired will be well within the knowledge of one skilled in the art and easily obtainable by following the more preferred aspects of this invention as explained more fully below and/or by simple routine experimentation.

For instance, the total gas pressure of hydrogen, carbon monoxide and olefinic unsaturated compound of the hydroformylation process of this invention may range from about 1 to about 10,000 psia. More preferably however the present process of this invention is operated at low pressures the preferred total gas pressure of hydrogen, carbon monoxide and olefinic unsaturated compound being less than about 1500 psia, more preferably less than about 500 psia and most preferably less than about 350 psia. While the minimum total pressure of the reactant gases is not particularly critical and is limited predominantly only by the amount of reaction gases necessary to obtain a desired rate of reaction the partial pressure of the carbon monoxide employed is known to have an effect on the sensitivity of rhodium complex catalysts and can lead to deactivation of the catalyst if said partial pressure is too high. Thus the preferred carbon monoxide partial pressure of the process of this invention is preferably less than about 200 psia, more preferably less than about 100 psia and most preferably from about 1 to about 50 psia. On the other hand the partial pressure of hydrogen gas of the hydroformylation process of this invention is preferably less than about 500 psia., more preferably less than about 400 psia and most preferably about 20 to about 200 psia. In addition it is generally preferred that the partial pressure of carbon monoxide be less than about 75 percent of the total gas pressure of (CO+H$_2$). However in certain instances it may be plausible to increase the carbon monoxide partial pressure to a value above about 75 percent of the total gas pressure. On the other hand in general a partial pressure attributable to hydrogen of from about 25 to 95 percent and more, based on the total gas pressure of (CO+H$_2$) should be suitable in most instances. It is further normally advantageous to employ a total gas pressure in which the partial pressure attributable to hydrogen is greater than the partial pressure attributable to carbon monoxide e.g. H$_2$/CO molar ratio of gaseous hydrogen to carbon monoxide any range from about 3:2 to 200:1 or higher, the more preferred hydrogen to carbon monoxide molar ratio being from about 3:2 to 20:1.

Further as noted above the hydroformylation process of this invention may be conducted at a reaction temperature from about 45° C. to about 200° C. The preferred reaction temperature employed in a given process will of course be dependent upon the particular olefinic starting material employed and the overall efficiency of hydroformylation desired. For instance in the hydroformylation of allyl alcohol to its desired straight chain aldehyde is preferred to employ a reaction temperature of about 45° C. to about 150° C. and most preferably about 60° C. to about 100° C. On the other hand reaction temperature of about 50° C. to about 145° C. and more preferably from about 90° C. to about 120° C. have been conventionally advanced for the hydroformylation of α-olefins and α,ω-dienes. While said reaction temperatures can be employed by the process of this invention, due to the high thermal stability of the rhodium-bisphosphine monooxide complex catalysts employed in the present invention it has been found that the overall efficiency of hydroformylating α-olefins and α,ω-dienes can be improved by carrying out the present reaction at even higher temperatures such as preferably from about 120° C. to about 200° C. and more preferably from about 125° C. to about 150° C.

Moreover the organic tertiary bisphosphine monooxide ligands employable in this invention as noted above are those having the general formula

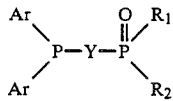

wherein Ar, $R_1$, $R_2$ and Y are as defined above. Such types of bisphosphine monooxides may be prepared by various conventional methods. For example a corresponding organic tertiary bisphosphine starting material can be oxidized with any suitable oxygenating agent such as oxygen or air, and the like to produce a mixture of monooxidized and dioxidized bisphosphines and the desired bisphosphine monooxide recovered and isolated from such mixtures by any suitable method such as crystallization, distillation, and the like. Another method for preparing bisphosphine monooxides which may be employed comprises the free radical addition of secondary phosphine oxides (e.g.

wherein $R_1$ and $R_2$ are as defined herein) with unsaturated tertiary phosphines (e.g. $Ar_2P-Y-CH=CH_2$ wherein Ar and Y are as defined herein) as disclosed e.g. in PCT, International Publication Number 80/01690 published Aug. 21, 1980. Alternative methods of preparing certain organic tertiary bisphosphine monooxides are found disclosed e.g. in U.S. Pat. No. 3,426,021, "Unsymmetrical Bis-Phosphorus Ligands", by S. O. Grim et al, *Inorganic Chemistry*, Vol. 14, pp. 656-660 (1975) and "Abnormal Hydrolysis of Cyclic Phosphonium Salts", by A. M. Aguiar et al, *J. Amer. Chem. Soc.*, Vol. 87, pp. 671-673 (1965).

More preferably the organic tertiary bisphosphine monooxide ligands employable in this invention can be prepared by the novel procedure disclosed in assignee's U.S. patent application Ser. No. 293,145 now U.S. Pat. No. 4,429,161 filed concurrently herewith. Said procedure comprises reacting a corresponding organic tertiary bisphosphine (e.g. $Ar_2P-Y-P-R_1R_2$ wherein Ar, $R_1$, $R_2$ and Y are as defined herein) with an organic monofunctional alkylating agent (e.g. a monovalent hydrocarbon halide such as an alkyl or aralkyl chloride, bromide or iodide, the preferred alkylating agent being benzyl bromide, in the presence of a suitable solvent for the bisphosphine starting material (e.g., a hydrocarbon solvent such as toluene) to form an insoluble monophosphonium salt of the bisphosphine starting material which can be easily recovered by any suitable method such as filtration. The intermediate monophosphonium salt is then hydrolyzed with an aqueous alkaline solution (e.g., 1 to 20 percent by weight of an alkali metal or alkaline earth metal hydroxide such as sodium hydroxide in water) to the desired organic tertiary bisphosphine monooxides employable in this invention. The bisphosphine monooxide product is a water insoluble precipitate that can be recovered by any suitable method such as filtration. Both procedural steps of said process are preferably conducted under nitrogen atmosphere and are essentially stoichiometric quantitative type reactions. However, while it is preferred to employ only about one mole of alkylating agent per mole of the bisphosphine starting material employed, it is preferred to employ an excess amount of water (e.g., from about a 100 percent stoichiometric excess on up to about a 10,000 percent stoichiometric excess or higher may be employed) in the hydrolysis step above that theoretical stoichiometric amount of water necessary to hydrolyze the monophosphonium salt to its desired bisphosphine monooxide product. The formation of the intermediate monophosphonium salt can be carried out at any suitable temperature such as from about 20° C. up to the boiling point of the solvent, while the hydrolysis procedure can also be carried out at any suitable temperature such as from about 20° C. to 100° C. This procedure is very efficient for preparing large yields of selectively desired bisphosphine monooxides and can be found more fully described in said Ser. No. 293,145, now U.S. Pat. No. 4,429,161 the entire disclosure of which is incorporated herein by reference thereto. Of course the organic tertiary bisphosphine starting materials and/or methods for their preparation are well known in the art.

Illustrative aryl radicals represented by the Ar groups in the above bisphosphine monooxide formulas include both substituted and unsubstituted aryl radicals. Such aryl radicals may contain from 6 to 12 carbon atoms, the most preferred aryl radical being phenyl, ($C_6H_5-$). Illustrative substituent groups that may be present on the aryl radicals, include e.g. alkyl radicals, alkoxy radicals, silyl radicals such as $-Si(R_5)_3$; amino radicals such as $-N(R_5)_2$; acyl radicals such as $-C(O)R_5$; carboxy radicals such as $-C(O)OR_5$; acyloxy radicals such as $-OC(O)R_5$; amido radicals such as $-C(O)N(R_5)_2$ and $-N(R_5)C(O)R_5$; sulfonyl radicals such as $-SO_2R_5$; ether radicals such as $-OR_5$, thionyl ether radicals such as $-SR_5$ as well as halogen, nitro, cyano, trifluoromethyl and hydroxy radicals, and the like, wherein each $R_5$ individually represents the same or different substituted or unsubstituted monovalent hydrocarbon radical having the same meaning as defined for $R_1$ and $R_2$ below, with the proviso that in amino substituents such as $-N(R_5)_2$, each $R_5$ taken together can also represent a divalent bridging group that forms a heterocyclic radical with the nitrogen atom and in amido substituents such as $C(O)N(R_5)_2$ and $-N(R_5)C(O)R_5$ each $-R_5$ bonded to N can also be hydrogen. Illustrative aryl radicals represented by Ar include e.g. phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl methoxyethylphenyl, acetamidophenyl, dimethylcarbamylphenyl, tolyl, xylyl, and the like. Most preferably both Ar radicals are phenyl.

Monovalent hydrocarbon radicals represented by $R_1$ and $R_2$, in the above formulas include those containing from 1 to 30 carbon atoms such as substituted or unsubstituted alkyl, aryl, alkaryl, aralkyl and alicyclic radicals. Among the more specific unsubstituted monovalent hydrocarbon radicals that may be mentioned are alkyl radicals including primary, secondary and tertiary alkyl radicals such as methyl, ethyl, n-propyl, isopropyl butyl, sec-butyl, t-butyl, t-butylethyl, t-butylpropyl, n-hexyl, amyl, sec-amyl, t-amyl, iso-octyl, decyl, dodecyl, octadecyl, eicosyl, and the like; aryl radicals such as phenyl, naphthyl and the like; aralkyl radicals such as benzyl, phenylethyl, triphenylmethylethane and the like, alkaryl radicals such as tolyl, xylyl, and the like; and alicyclic radicals such as cyclopentyl, cyclohexyl, cyclooctyl, cyclohexylethyl, and the like. In addition such monovalent hydrocarbon radicals may be substituted with any substituent which does not unduly adversely effect the process of this invention. Suitable illustrative substitutents that may be on the hydrocarbon radical are for example silyl radicals such as —Si($R_5$)$_3$; amino radicals such as —N($R_5$)$_2$; acyl radicals such as —C(O)$R_5$: acyloxy radicals such as —OC(O)$R_5$; amido radicals such as —C(O)N($R_5$)$_2$ and —N($R_5$)C(O)$R_5$; sulfonyl radicals such as —SO$_2R_5$; ether radicals such as —O$R_5$, thionyl ether radicals such as —S$R_5$ as well as halogen, nitro, cyano, trifluoromethyl and hydroxy radicals, and the like, wherein each $R_5$ individually represents the same or different substituted or unsubstituted monovalent hydrocarbon radical having the same meaning as defined for $R_1$ and $R_2$, with the proviso that in amino substituents such as —N($R_5$)$_2$, each $R_5$ taken together can also represent a divalent bridging group that forms a heterocyclic radical with the nitrogen atom and in amido substituents such as C(O)N($R_5$)$_2$ and —N($R_5$)C(O)$R_5$ each $R_5$ bonded to N can also be hydrogen. Illustrative substituted monovalent hydrocarbon radicals include e.g.,

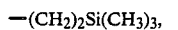 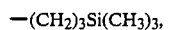
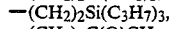 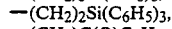
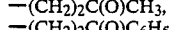 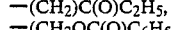
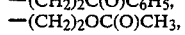 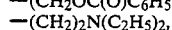
 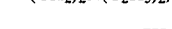

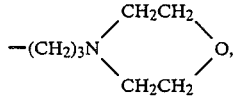 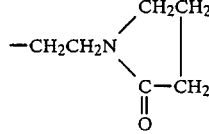

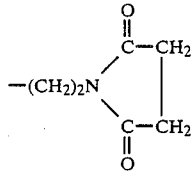  —(CH$_2$)$_2$CONH$_2$,

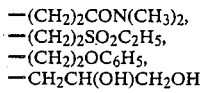 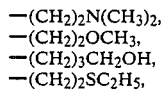

—(CH$_2$)$_3$SC$_6$H$_5$, as well as fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl, furyl, pyrryl, methoxyethylphenyl, acetamidophenyl, dimethylcarbamylphenyl, and the like.

The more preferred substituted and unsubstituted monovalent hydrocarbon radicals represented by $R_1$ and $R_2$ and $R_5$ are alkyl radicals having from 1 to 12 carbon atoms and aryl radicals having from 6 to 12 carbon atoms, the most preferred radicals being unsubstituted monovalent hydrocarbon radicals and the most preferred aryl radical being phenyl.

In general the more preferred organic tertiary bisphosphine monooxides are those such as wherein $R_1$ and $R_2$ both represent an aryl radical, especially phenyl (C$_6$H$_5$—).

The divalent bridging group represented by Y in the above formulas is a divalent radical containing from 1 to 30 carbon atoms selected from the group consisting of hydrocarbon radicals, oxygen containing hydrocarbon radicals (i.e. hydrocarbon radicals interrupted with an oxygen atom), sulfur containing hydrocarbon radicals (i.e. hydrocarbon radicals interrupted with a sulfur atom) and nitrogen containing hydrocarbon atoms (i.e. hydrocarbon radicals interrupted with a nitrogen atom). Preferably such radicals contain from 1 to 12 carbon atoms. Illustrative divalent hydrocarbon radicals include alkylene radicals (e.g. methylene (—CH$_2$—), ethylene, propylene, isopropylene, butylene, 1,2-dimethylethylene, t-butylene, neopentylene, 2-methyl-propylene, hexylene, 2-ethylhexylene, dodecylene, eicosylene, and the like); arylene radicals (e.g. phenylene, diphenylene, and the like; as well as alkylene containing arylene radicals (e.g. methylene-phenylene (—CH$_2$C$_6$H$_4$—), ethylenephenylethylene (—C$_2$H$_4$C$_6$H$_4$—C$_2$H$_4$—), phenylenepropylphenylene (—C$_6$H$_4$C(CH$_3$)$_2$C$_6$H$_4$—), and the like); alkylidene radicals (e.g. ethylidene (—CH=CH—), and the like)); and the like. Illustrative oxygen containing hydrocarbon radicals include alkyleneoxyalkylene radicals (e.g. ethyleneoxymethylene (—C$_2$H$_4$OCH$_2$—), propyleneoxymethylene (—C$_3$H$_6$OCH$_2$—), ethyleneoxyethylene (—C$_2$H$_4$OC$_2$H$_4$—), 1,2-bis(ethyleneoxy)ethane (—C$_2$H$_4$OC$_2$H$_4$OC$_2$H$_4$—), propyleneoxypropylene (—C$_3$H$_6$OC$_3$H$_6$—) and the like)); aryleneoxyalkylene radicals (e.g. phenyleneoxymethylene (—C$_6$H$_4$OCH$_2$—), and the like); and the like. Illustrative sulfur or thio containing hydrocarbon radicals include alkylenethioalkylene radicals (e.g. ethylenethioethylene (—C$_2$H$_4$SC$_2$H$_4$—), 1,2-bis(ethylenethio)ethane (—C$_2$H$_4$SC$_2$H$_4$SC$_2$H$_4$—), propylenethiomethylene (—C$_3$H$_6$SCH$_2$—), propylenethiopropylene (—C$_3$H$_6$SC$_3$H$_6$—), and the like)); arylenethioalkylene radicals (e.g. phenylenethiomethylene (—C$_3$H$_6$S—CH$_2$—), and the like); and the like. Illustrative amino containing hydrocarbon radicals include alkyleneaminoalkylene radicals (e.g., methyleneaminomeethylethylene (—CH$_2$N(CH$_3$)C$_2$H$_4$—), ethyleneaminomethylethylene (—C$_2$H$_4$N(CH$_3$)C$_2$H$_4$—), bis(ethyleneaminomethyl)ethane (—C$_2$H$_4$N(CH$_3$)C$_2$H$_4$N(CH$_3$)C$_2$H$_4$—), propyleneaminomethylpropylene (—C$_3$H$_6$N(CH$_3$)C$_3$H$_6$—) and the like); and the like. Preferably Y is a divalent hydrocarbon radical, especially a divalent alkylene radical containing from 2 to 8 carbon atoms.
Illustrative examples of such organic ditertiary bisphosphine monooxides include, e.g.
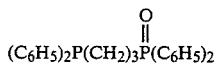
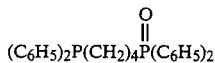
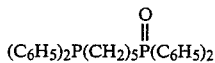
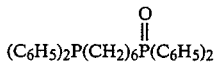
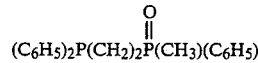
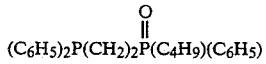
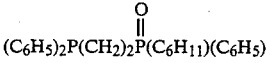
cis 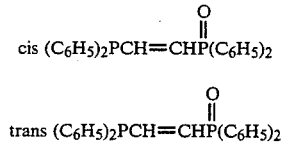
trans (C₆H₅)₂PCH=CHP(C₆H₅)₂
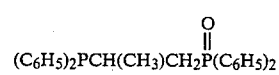
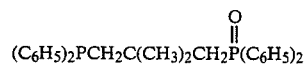
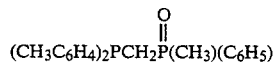
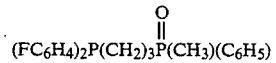
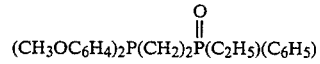
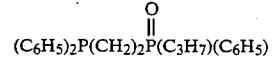
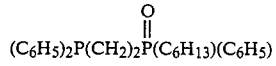
-continued
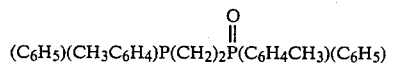
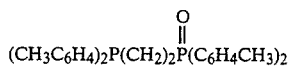
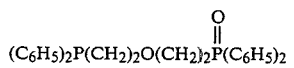
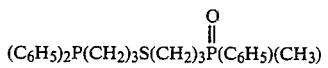
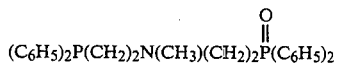
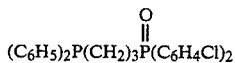
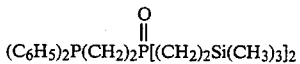
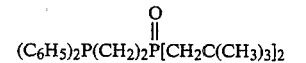
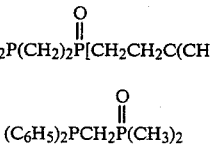
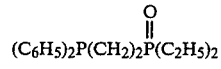
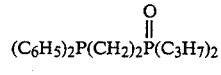
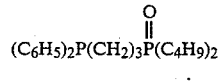
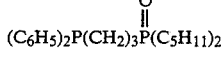
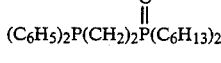
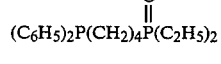
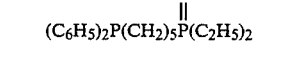
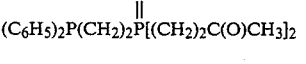
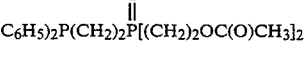

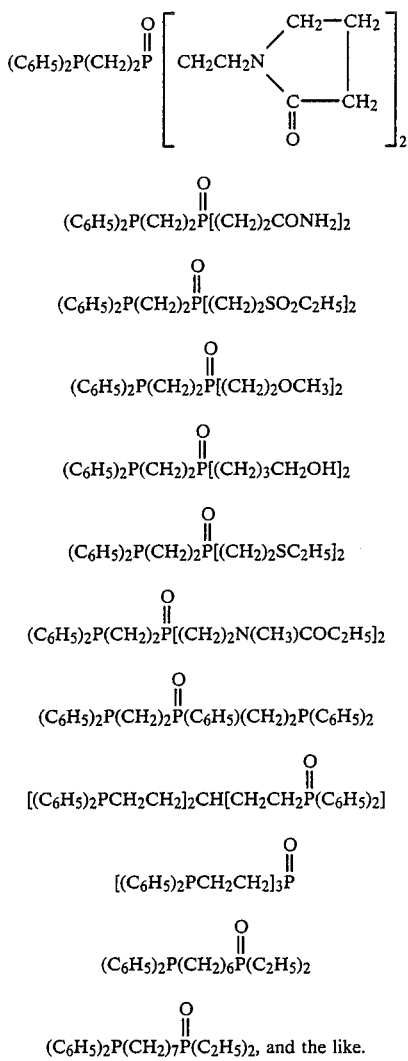

$(C_6H_5)_2P(CH_2)_2\overset{O}{\overset{\|}{P}}[(CH_2)_2CONH_2]_2$ $(C_6H_5)_2P(CH_2)_2\overset{O}{\overset{\|}{P}}[(CH_2)_2SO_2C_2H_5]_2$ $(C_6H_5)_2P(CH_2)_2\overset{O}{\overset{\|}{P}}[(CH_2)_2OCH_3]_2$ $(C_6H_5)_2P(CH_2)_2\overset{O}{\overset{\|}{P}}[(CH_2)_3CH_2OH]_2$ $(C_6H_5)_2P(CH_2)_2\overset{O}{\overset{\|}{P}}[(CH_2)_2SC_2H_5]_2$ $(C_6H_5)_2P(CH_2)_2\overset{O}{\overset{\|}{P}}[(CH_2)_2N(CH_3)COC_2H_5]_2$ $(C_6H_5)_2P(CH_2)_2\overset{O}{\overset{\|}{P}}(C_6H_5)(CH_2)_2P(C_6H_5)_2$ $[(C_6H_5)_2PCH_2CH_2]_2CH[CH_2CH_2\overset{O}{\overset{\|}{P}}(C_6H_5)_2]$ $[(C_6H_5)_2PCH_2CH_2]_3\overset{O}{\overset{\|}{P}}$ $(C_6H_5)_2P(CH_2)_6\overset{O}{\overset{\|}{P}}(C_2H_5)_2$ $(C_6H_5)_2P(CH_2)_7\overset{O}{\overset{\|}{P}}(C_2H_5)_2$, and the like.

As noted above the organic tertiary bisphosphine monooxide ligands defined above are employed in this invention as both the phosphorus ligand of the rhodium-phosphorus complex catalyst of the hydroformylation process of this invention as well as the free phosphorus ligand present in the reaction medium of the hydroformylation process of this invention. In addition it is to be understood that while the phosphorus ligand of the rhodium-phosphorus complex catalyst and the excess free phosphorus ligand present in a given process of this invention are normally of the same type of bisphosphine monooxide, different types of bisphosphine monooxides as well as, mixtures of two or more different bisphosphine monooxides may be employed for each purpose in any given process if desired.

While it is not intended to limit the present invention by any single explanation as to the exact nature of the active rhodium-bisphosphine monooxide complex catalyst or by any single theory or mechanistic discourse of how the rhodium is complexed with the bisphosphine monooxide, it appears that the active catalyst in its simplest form consists essentially of a concentration of organic tertiary bisphosphine monooxide ligand and carbon monoxide equal to a total of four moles in complex combination with one mole of rhodium. Of course it is to be understood that the term "complex" means a coordination compound formed by the union of one or more electronically rich molecules or atoms capable of independent existence with one or more electronically poor molecules or atoms, each of which is also capable of independent existence. Thus the active species may comprise a complex catalyst mixture, in their monomeric forms, which are characterized by one, two and/or three bisphosphine monooxide molecules complexed with one molecule of rhodium. As can be surmised from the above discussion, carbon monoxide (which is also properly classified as a ligand) is likewise present and complexed with the rhodium in the active species. Furthermore, the active catalyst species may also contain hydrogen as a ligand. Thus the ultimate composition of the active complex species can be likened or attributed to the outcome of competing reactions between carbon monoxide and the bisphosphine monooxide ligand for "complexing sites" with the rhodium element and these competing reactions can be disturbed or influenced, within significant limits, by increasing or decreasing the partial pressure due to carbon monoxide, or by increasing or decreasing the concentration of the bisphosphine monooxide ligand. As a generalized statement therefore, the component (carbon monoxide or bisphosphine monooxide ligand) which can shift the equilibrium of the competing reaction in its favor should enjoy the greater opportunities of occupying the "complexing sites" with rhodium to give the active complex catalyst. Moreover one could view the function of the free organic tertiary bisphosphine monooxide ligand as either maintaining the status quo of the various forms of active complex catalyst during the hydroformylation, or as a means for shifting the equilibrium of the competing reactions in its favor and therefore causing additional bisphosphine monooxide ligand to enter into the complex combination with rhodium with the probable eviction of a similar number of carbon monoxide ligands from the complex catalyst. In addition it has been discovered that unlike prior art monophosphine ligands, e.g. triphenylphosphine, the organic tertiary bisphosphine monooxide ligands of this invention are weakly chelated to the rhodium through this phosphorus-monooxide groups (e.g.

in addition to being strongly coordinated to the rhodium through their non-oxygenated phosphorus groups (e.g. Ar₂P—). Thus by way of illustration of the active complex catalysts of this invention may be represented by the generalized formula

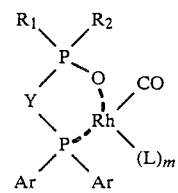

wherein Ar, R₁R₂ and Y are the same as defined herein, CO represents carbon monoxide, m is an integer of from 1 to 2 and each L individually represents an identical or different ligand, e.g. hydrogen, carbon monoxide and- /or organic tertiary bisphosphine monooxide. Moreover as is the case with prior art rhodium-phosphorus hydroformylation complex catalysts, the rhodium-bisphosphine monooxide complex catalysts of this invention may be formed by methods known in the art. For example preformed stable rhodium hydridocarbonyltris(organic tertiary bisphosphine monooxide) catalysts may be introduced into the reaction medium of the hydroformylation process. Such preformed catalysts may be prepared by reacting conventional trisorganophosphine rhodium carbonyl hydrides e.g. hydridorhodiumcarbonyltristriphenylphosphine, with an organic tertiary bisphosphine monooxide ligand as defined herein in the presence of a suitable hydrocarbon solvent to effect a phosphorus ligand interchange. Alternatively, and this is preferred, the rhodium-bisphosphine monooxide complex catalysts of this invention can be derived from a rhodium catalyst precursor such as rhodium dicarbonyl acetylacetonate, $RhO_3$, $Rh_4(CO)_2$, $Rh_6(CO)_{16}$, $Rh(NO_3)_3$ and the like which may be introduced into the reaction medium along with the bisphosphine monooxide ligand for the in situ formation of active catalyst. In a preferred embodiment rhodium dicarbonyl acetylacetonate is employed as a rhodium precursor and reacted in the presence of a solvent with the organic tertiary bisphosphine monooxide to form a catalytic rhodium carbonyl organic tertiary bisphosphine monooxide acetylacetonate precursor which is introduced into the reactor along with excess free organic tertiary bisphosphine monooxide ligand for the in situ formation of the active catalyst. In any event it is sufficient for the purpose of this invention to understand that carbon monoxide, hydrogen and organic tertiary bisphosphine monooxide are all ligands that are capable of being complexed with the rhodium and that an active rhodium-bisphosphine monooxide complex catalyst is present in the reaction medium under the conditions of hydroformylation.

Accordingly more specifically the rhodium-bisphosphine monooxide complex catalysts of this invention may be defined as consisting essentially of rhodium complexed with carbon monoxide and an organic tertiary bisphosphine ligand as defined herein. Of course it is to be understood that the catalyst terminology "consisting essentially of" is not meant to exclude, but rather include, hydrogen complexed with the rhodium, in addition to carbon monoxide and the bisphosphine monooxide ligand. However, such terminology is meant to exclude other materials in amounts which unduly adversely poison or unduly deactivate the catalyst and thus most desirably is free of contaminants such as rhodium-bound halogen e.g. chlorine, and the like. The hydrogen and/or carbonyl ligands of an active rhodium-bisphosphine monooxide complex catalyst may be present as a result of being ligands bonded to a precursor catalyst and/or as a result of in situ formation due to the hydrogen and carbon monoxide gases employed in the hydroformylation process. Likewise as in the case of continuous hydroformylation process that has employed a rhodium triaryl phosphine catalyst which results in the in situ formation of alkyl substituted arylphosphine ligands as explained in U.S. Pat. No. 4,260,828 during the hydroformylation process, it may be possible that some alkyl substituted aryl bisphosphine monooxides (i.e. ligands wherein one the aryl groups of the $Ar_2P$ group of the originally employed bisphosphine monooxide ligand has been replaced by an alkyl radical e.g. corresponding to the olefinically unsaturated starting material to be hydroformylated) are produced in situ in the hydroformylation process of this invention. Thus it should be understood that the active rhodium-bisphosphine monooxide catalyst of this invention and the catalyst terminology "consisting essentially of" is also not meant to exclude, but include the possible presence of such types of alkyl substituted aryl bisphosphine monooxide ligands complexed to the rhodium as well as the other above mentioned complexing ligands.

Moreover like the prior art rhodium-phosphorus complex hydroformylation catalyst, it is clear that the amount of rhodium-bisphosphine monooxide complex catalyst present in the hydroformylation medium of the process of this invention need only be that minimum amount which is necessary to provide the rhodium concentration (which concentration in general may range from about 25 ppm to about 1000 ppm, and more preferably from about 50 to about 400 ppm of rhodium calculated as free metal) desired to be employed and which will, furnish the basis for at least that catalytic amount of rhodium necessary to catalyze the particular hydroformylation process desired.

The olefinically unsaturated organic compounds that may be hydroformylated by the process of this invention are olefinic compounds that may contain from 2 to 20 carbon atoms characterized by a terminal ethylenic carbon-to-carbon bond which may be a vinylidene group, i.e.

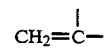

or a vinyl group, i.e. $CH_2=CH-$. They may be straight-chain or branched chain and may contain groups or substitutents which do not essentially interfere with the course of the process of this invention. Such groups and substituents can be illustrated by carbonyl

carbonyloxy

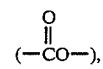

oxy (—O—), hydroxy (—OH), carboxy (—COOH), halo, alkoxy, phenyl, haloalkyl, and the like. The olefinic compound can contain one ethylenic bond or it can contain more than one terminal ethylene bond. Such olefinically unsaturated organic compounds are well known in the art.

Illustrative olefinic starting materials for the process of this invention include e.g. ethylene, propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, allyl acetate, 1,3-butadiene, 1,5,-hexadiene, 1,7-octadiene, 1,9-decadiene, 1,4-hexadiene, 3-cyclohexyl-1-butene, allyl alcohol, hex-1-en-4-ol, oct-1-en-4-ol, vinyl acetate, allyl-t-butyl ether, vinylpropionate, allyl propionate, allyl butyrate, methyl methacrylate, 3-butenyl acetate, vinyl ethyl ether, vinyl methyl ether, allyl ethyl ether, n-propyl-7-octenoic acid, 3-butenenitrile, 5-hexenamide, and the like.

The more preferred olefinic compounds are alpha olefinic compounds containing from 2 to 20 carbon atoms such as alkenes, alkyl alkenoates, alkenyl alkanoates, alkenyl alkyl ethers and alkenols. The most preferred olefinic starting materials are alpha alkenes containing from 4 to 20 carbon atoms and functional olefins, such as allyl alcohol and alpha,omega dienes, containing from 4 to 20 carbon atoms.

As noted above the hydroformylation process of this invention is further carried out in the presence of free bisphosphine monooxide ligand, i.e. ligand that is not tied or complexed with the rhodium of the rhodium complex catalyst. Thus said free bisphosphine monooxide ligand may correspond to any of the above defined organic tertiary bisphosphine monooxides discussed above. However while it is preferred to employ a free bisphosphine monooxide ligand that is the same as the bisphosphine monooxide ligand of the rhodium-phosphorus complex catalyst such ligands need not be the same in a given process, but can be different if desired. Moreover it has been found that less free bisphosphine monooxide ligand than prior art monophosphine type ligands is. generally required to achieve comparable and/or more desirable results in terms of straight chain aldehyde process efficiency. For example while it is generally most preferred in the prior art to employ at least about 100 moles of free triphenylphosphine per mole of rhodium-triphenylphosphine complex catalyst it has been found that excellent straight chain aldehyde product efficiencies can be achieved by employing less than 100 moles of free bisphosphine monooxide ligand per mole of rhodium-bisphosphine monooxide complex catalyst. Thus while the hydroformylation process of this invention can be carried out in any excess amount of free bisphosphine monooxide ligand desired, e.g. at least one mole of free monooxide ligand per mole of catalytically active rhodium present in the hydroformylation medium, in general molar amounts of free bisphosphine monooxide ligand from about 3 to about 80 moles per mole of catalytically active rhodium present in the hydroformylation medium should be suitable for most purposes.

Likewise the hydroformylation process of this invention is also preferably conducted in the presence of an organic solvent for the rhodium-bisphosphine monooxide catalyst. Any suitable solvent which does not unduly adversely interfere with the intended hydroformylation process can be employed. Such solvents may include those heretofore commonly employable in known hydroformylation processes such as e.g. disclosed in U.S. Pat. Nos. 3,527,809 and 4,148,830. Of course mixtures of one or more different catalytic solvents may be employed if desired. In general it is preferred to employ aldehyde compounds corresponding to the aldehyde products desired to be produced (e.g. n-butyraldehyde) and/or higher boiling aldehyde condensation by-products as the primary solvent such as the higher boiling aldehyde liquid condensation by-products that are produced in situ during the hydroformylation process (e.g. butyraldehyde trimers). Such aldehyde condensation products can also be preformed if desired and used accordingly. Moreover such higher boiling aldehyde condensation by-products and methods for their preparation are more fully described in U.S. Pat. Nos. 4,148,830 and 4,247,486. Of course it is obvious that the amount of solvent employed is not critical to the subject invention and need only be that amount sufficient to provide the hydroformylation reaction medium with the particular rhodium concentration desired for said hydroformylation process. In general the amount of solvent when employed may range from about 5 percent by weight up to about 95 percent by weight or more based on the total weight of the hydroformylation reaction medium.

It is generally preferred to carry out the hydroformylation process of this invention in a continuous manner. Such continuous hydroformylation processes are well known in the art and may involve the recycling of a rhodium catalyst containing solution separated from the reaction product or a gas recycle procedure.

A further aspect of this invention can be described as a catalyst precursor composition consisting essentially of a solubilized rhodium carbonyl bisphosphine monooxide acetylacetonate complex precursor catalyst, an organic solvent and free organic tertiary bisphosphine monooxide. Such precursor compositions are prepared by forming a solution of rhodium dicarbonyl acetylacetonate, an organic solvent and an organic tertiary bisphosphine monooxide as defined herein. The bisphosphine monooxide readily replaces one of the dicarbonyl ligands of the rhodium-acetylacetonate complex precursor at room temperature as witnessed by the evolution of carbon monoxide gas. This substitution reaction may be facilitated by heating the solution if desired. Any suitable organic solvent in which both the rhodium-dicarbonyl acetylacetonate complex precursor and rhodium carbonyl bisphosphine monooxide acetylacetonate complex precursor are soluble can be employed. Suitable solvents of course include and are preferably those employable in the hydroformylation process of this invention. Accordingly the amounts of rhodium complex catalyst precursor, organic solvent and bisphosphine monooxide, as well as their preferred embodiments present in such catalyst precursor compositions may obviously correspond to those amounts employable in the hydroformylation process of this invention and which have already been discussed herein above. Experience has shown that the acetylacetonate ligand of the precursor catalyst is very quickly replaced, within a matter of minutes, after the hydroformylation process has begun with a different ligand e.g. hydrogen, carbon monoxide or bisphosphine monooxide, to form the active rhodium complex catalyst as explained above. The acetylacetone which is quickly freed from the precursor catalyst under hydroformylation conditions is removed from the reaction medium with the product aldehyde and thus is in no way detrimental to the hydroformylation process. The use of such preferred rhodium complex catalytic precursor compositions thus provides a simple economical and efficient method for handling the rhodium precursor metal and hydroformylation start-up.

The use of the bisphosphine monooxide ligands for the purposes explained above have been found particularly beneficial in the hydroformylation of α-olefins having from 4 to 20 carbon atoms as well as allyl alcohol and α,ω-dienes having from 4 to 20 carbon atoms in that the overall processing efficiency in providing desired straight chain aldehyde product is greatly increased by said use over that obtainable when employing conventional prior art monophosphine ligands such as triphenylphosphine. For example the use of bisphosphine monooxides have been found to greatly curtail such undesirable side reactions such as hydrogenation of the starting olefinic compound to its corresponding saturated alkane and/or isomerization of the starting olefinic compound to an internal olefin as compared to those results obtained when a conventional phosphorus ligand such as triphenylphosphine is employed.

Finally, the aldehyde products of the hydroformylation process of this invention have a wide range of utility that is well known and documented in the prior art e.g. they are especially useful as starting materials for the production of alcohols.

The following examples are illustrative of the present invention and are not to be regarded as limitative. It is to be understood that all of the parts, percentages and proportions referred to herein and in the appended claims are by weight unless otherwise indicated.

EXAMPLES 1 TO 10

A series of various rhodium complex catalyst precursor solutions consisting essentially of solubilized rhodium carbonyl phosphorus acetylacetonate complex precursor catalyst, organic solvent and free organic phosphorus ligand were prepared and employed to hydroformylate hexene-1 into heptanal in the following manner.

Rhodium dicarbonyl acetylacetonate was mixed with sufficient phosphorus ligand (said ligand being varied in each instance as shown in TABLE I below) and diluted with sufficient solvent mixture (a 2:1 volume ratio) of bis-2-(ethoxyethyl)ether to 1,4-butanediol to produce a rhodium catalytic precursor solution containing about 200 ppm rhodium and about 40 moles of said employed phosphorus ligand per mole of rhodium.

Each rhodium catalytic precursor solution so prepared was then employed to hydroformylate hexene-1 in a 100 ml. stainless steel autoclave equipped with a magnetic stirrer and an electrical band heater having a proportional temperature controller. The internal temperature was monitored with a platinum resistance thermometer of $\pm 0.1°$ C. accuracy. The autoclave was connected to a gas manifold for initial pressurization with the carbon monoxide and hydrogen reactant gases. An external reservoir of 0.5 liter capacity containing a 1:1 molar mixture of carbon monoxide and hydrogen was also connected to the autoclave by means of a motor valve. The autoclave was also equipped with a 100 to 135 psi. pressure transmitter. During hydroformylation the autoclave was maintained at about 120 psig. via the external reservoir/motor value/pressure transmitter.

In each hydroformylation reaction, about 20 ml. of the rhodium catalytic precursor solution so prepared containing the rhodium complex, the phosphorus ligand and the solvent was charged to the autoclave and flushed with nitrogen by means of the gas manifold. The rhodium catalytic precursor solution was maintained under about 5 psig. nitrogen and heated to about 80° C. The nitrogen pressure was reduced to about 5 psi. and 6 ml. of hexene-1 was syringed into the autoclave. About 12 psia. of carbon monoxide gas along with about 96 psia. of hydrogen gas was added to arrive at a total pressure of about 120 psig. and stirring started. Carbon monoxide and hydrogen started being consumed immediately and were replenished from said external reservoir through the motor valve-pressure transmitter assembly.

The hydroformylation reaction rate in gram moles per liter per hour of heptaldehydes produced was calculated from the steady rate of pressure drop in the external reservoir, while the mole ratio of linear to branched heptanal product was measured by gas chromatography and the results are given in TABLE I below, said results being determined after about a 10 to 20 percent conversion of the hexene-1 starting material.

TABLE I

| Example No. | Phosphorus Ligand | Reaction Rate Gram Moles/ Liter Hour | Linear/ Branched Heptanal Mole Ratio |
|---|---|---|---|
| 1. | $(C_6H_5)_2PCH_2\overset{O}{\overset{\|}{P}}(C_6H_5)_2$ | 0.61 | 9.4 |
| 2. | $(C_6H_5)_2P(CH_2)_2\overset{O}{\overset{\|}{P}}(C_6H_5)_2$ | 0.53 | 33.8 |
| 3. | $(C_6H_5)_2P(CH_2)_3\overset{O}{\overset{\|}{P}}(C_6H_5)_2$ | 1.03 | 22.9 |
| 4. | $(C_6H_5)_2P(CH_2)_4\overset{O}{\overset{\|}{P}}(C_6H_5)_2$ | 0.96 | 25.8 |
| 5. | $(C_6H_5)_2P(CH_2)_5\overset{O}{\overset{\|}{P}}(C_6H_5)_2$ | 2.23 | 15.5 |
| 6. | $(C_6H_5)_2P(CH_2)_6\overset{O}{\overset{\|}{P}}(C_6H_5)_2$ | 1.46 | 9.1 |
| 7. | CIS $(C_6H_5)_2PCH=CH\overset{O}{\overset{\|}{P}}(C_6H_5)_2$ | 0.45 | 5.1 |
| 8. | TRANS $(C_6H_5)_2PCH=CH\overset{O}{\overset{\|}{P}}(C_6H_5)_2$ | 1.27 | 3.2 |
| 9. | $(C_6H_5)_3P$ | 2.70 | 19.6 |
| 10. | $(C_6H_5)_2PC_3H_7$ | 1.67 | 10.9 |

The above data demonstrates the significant advantage of certain ligands of the present invention (Examples 1 to 6) regarding their property to give high linear/branched aldehyde selectivity. Examples 9 and 10 are included for comparison purposes and are not within the scope of the invention. For instance the bisphosphine monooxide ligand of Example 2 gave a far greater linear/branched aldehyde selectivity than either the triphenylphosphine ligand of Example 9 or the propyldiphenylphosphine ligand of Example 10.

EXAMPLES 11 TO 16

The procedure in Examples 1 to 10 was repeated to hydroformylate hexene-1 save for using the various phosphorus ligands shown in TABLE II and varying the number of moles of phosphorus ligand employed per mole of rhodium from about 40:1 to about 20:1. The hydroformylation reaction rate in terms of gram moles per liter per hour of heptaldehydes produced as well as the mole ratio of linear to branched heptanal product were determined in the same manner as Examples 1 to 10 and the results are given in TABLE II below.

TABLE II

| Example No. | Phosphorus Ligand | P/Rh Mole Ratio | Reaction Rate Gram Moles/ Liter Hour | Mole Ratio Linear/ Branched Heptanal |
|---|---|---|---|---|
| 11. | $(C_6H_5)_3P$ | 40 | 2.7 | 19.6 |
| 12. | $(C_6H_5)_3P$ | 20 | 3.8 | 5.8 |
| 13. | $(C_6H_5)_2PC_3H_7$ | 40 | 1.7 | 10.9 |
| 14. | $(C_6H_5)_2PC_3H_7$ | 20 | 2.1 | 4.7 |
| 15. | $(C_6H_5)_2P(CH_2)_2\overset{\overset{O}{\|}}{P}(C_6H_5)_2$ | 40 | 0.5 | 33.8 |
| 16. | $(C_6H_5)_2P(CH_2)_2\overset{\overset{O}{\|}}{P}(C_6H_5)_2$ | 20 | 1.5 | 9.8 |

Examples 11 to 14 are given here for comparison. They show that using triphenylphosphine or propylidiphenylphosphine at low phosphine/rhodium molar ratio give much lower linear/branched aldehyde ratios than the bisphosphine monooxide ligand of Examples 15 and 16 representing the present invention.

EXAMPLES 17 TO 19

The procedure in Examples 1 to 10 was repeated to hydroformylate hexene-1 save for using the phosphorus ligands shown in TABLE III below and the hydroformylation reactions were carried out to completion, i.e. full conversion (consumption) of the hexene-1-starting material. The analysis of the completed hydroformylation reaction product solution for each example in terms of the gas chromatographic area percents of isomerized cis and trans hexene-2 by-products and of the linear and branched heptanal products as well as the linear aldehyde product selectivity which is determined by dividing the area percent of linear heptanal product by the sum of the area percents of the branched heptanal, cis and trans hexene-2 products is given in TABLE III below.

Example 18 as shown by the far higher linear aldehyde product selectivity obtained in Example 19. Thus more linear aldehyde product may be produced per given amount of olefin starting material using the bisphosphine monooxide ligand of Example 19 than with either triphenylphosphine ligand or propyldiphenylphosphine ligand.

EXAMPLES 20–21

In a similar manner as described in Examples 1 to 10 allyl alcohol was hydroformylated using the following conditions.

The rhodium catalytic precursor solution of Example 20 contained about 100 ppm rhodium (calculated as free metal and introduced as $Rh(CO)_2$ acetylacetonate) and about 238 moles of triphenylphosphine ligand per mole of rhodium in dimethylformamide solvent, while the precursor solution of Example 21 was the same save for the fact that it contained about 68 ppm rhodium and employed the monooxide of bisdiphenylphosphino ethane as the phosphorus ligand. The hydroformylation temperature was about 80° C. and the hydroformylation conducted at a total gas pressure of about 110 psi. the

TABLE III

| Example No. | Phosphorus Ligand | *Hexene-2 Trans | *Hexene-2 Cis | *Heptanal Linear | *Heptanal Branched | **Linear Aldehyde Product Selectivity |
|---|---|---|---|---|---|---|
| 17. | $(C_6H_5)_3P$ | 10.3 | 2.6 | 74.3 | 12.8 | 2.9 |
| 18. | $(C_6H_5)_2PC_3H_7$ | 5.1 | 1.0 | 77.4 | 16.5 | 3.4 |
| 19. | $(C_6H_5)_2P(CH_2)_2\overset{\overset{O}{\|}}{P}(C_6H_5)_2$ | 6.6 | 0.7 | 84.1 | 8.6 | 5.3 |

*Gas chromatographic area percents normalized to 100
**Gas chromatographic area percent of linear heptanal divided by the sum of the gas chromatographic area percents of branched heptanal, cis and trans hexene-2.

The above data shows that Example 19 using a bisphosphine monooxide ligand gave only about half the rate of hexene-1 isomerization to hexene-2 than that of Example 17 using triphenylphosphine ligand and about equal to that of Example 18 using propyldiphenylphosphine ligand. This property together with the high linear/branched aldehyde ratio obtained with the bisphosphine monooxide of Example 19 results in a higher processing (chemical) efficiency to linear aldehyde product than obtained with either the triphenylphosphine of Example 17 or the propyldiphenylphosphine of partial pressure of hydrogen to carbon monoxide gas ratio being about 2:1 for each example. The results given in TABLE IV below and show the gas chromatographic area percents of linear ($HOCH_2CH_2CH_2CHO$) and branched ($CH_3CH(CHO)CH_2OH$) aldehyde products and propionaldehyde (an isomerization by-product), as well as the linear ($HOCH_2CH_2CH_2CHO$) aldehyde product selectivity of each example. Said results were determined after the hydroformylation reactions had proceeded to about a 20 percent conversion of the allyl alcohol starting material.

TABLE IV

| Example No. | Phosphorus Ligand | *Aldehyde Product Linear | *Aldehyde Product Branched | *Propionaldehyde By-Product | **Linear Aldehyde Product Selectivity |
|---|---|---|---|---|---|
| 20 | $(C_6H_5)_3P$ | 74.9 | 9.4 | 15.7 | 3 |
| 21 | $(C_6H_5)_2P(CH_2)_2\overset{O}{\overset{\|}{P}}(C_6H_5)_2$ | 82.0 | 16.3 | 1.7 | 4.5 |

*Gas chromatographic area percents normalized to 100
**Gas chromatographic area percent of linear aldehyde divided by the sum of the gas chromatographic area percents of branched aldehyde and propinonaldehyde by-product.

The above data shows that the bisphosphine monooxide ligand of Example 21 was far superior in reducing the amount of isomerized propionaldehyde by-product than the triphenylphosphine ligand of Example 20.

EXAMPLES 22 TO 26

A series of various rhodium complex catalyst precursor solutions consisting essentially of solubilized rhodium carbonyl phosphorus acetylacetonate complex precursor catalyst, organic solvent and free organic phosphorus ligand were prepared and employed to hydroformylate 1,5-hexadiene into suberic aldehyde in the following manner.

Rhodium dicarbonyl acetylacetonate was mixed with sufficient phosphorus ligand (said ligand being varied in each instance as shown in TABLE V below) and diluted with sufficient dimethylformamide solvent to produce a rhodium catalytic precursor solution containing about 340 ppm rhodium and about 30 moles of said employed phosphorus ligand per mole of rhodium.

In each hydroformylation reaction, about 10 ml. of the rhodium catalytic precursor solution so prepared was charged to an autoclave as described in Examples 1 to 10. The precursor solution was maintained under nitrogen and heated to about 80° C. About 60 psi. of carbon monoxide and hydrogen in a 1:1 mole ratio was added and maintained for about one-half hour. The reactor was then purged with nitrogen and about 5 ml. of 1,5-hexadiene added. The pressure was then brought to about 120 psig. with about 45 psig. nitrogen and about 75 psi of carbon monoxide and hydrogen in a 1:1 molar ratio. During hydroformylation the autoclave was maintained at about 120 psig. via the external reservoir of premixed $CO/H_2$ (1:1 molar ratio) motor valve and pressure transmitter. The hydroformylation reaction rate in gram moles per liter per hour of aldehydes produced was calculated from the steady rate of pressure drop in the external reservoir, while the linear $C_8$-dialdehyde (suberic aldehyde) efficiency was determined by dividing the gas chromatographic area percent of linear $C_8$-dialdehyde by the sum of the gas chromatographic area percents of all aldehydes (mono, di, linear and branched) times 100, as measured on the completed reaction product solution (i.e. full conversion of the 1,5-hexadiene starting material. The results of said analysis are given in TABLE V below.

TABLE V

| Example No. | Phosphorus Ligand | Reaction Rate Gram Moles/ Liter Hour | Linear $C_8$—Dialdehyde Product Efficiency* |
|---|---|---|---|
| 22 | $(C_6H_5)_2P(CH_2)_2\overset{O}{\overset{\|}{P}}(C_6H_5)_2$ | 5.0 | 58 |
| 23 | $(C_6H_5)_2PC_2H_5$ | 3.9 | 52 |
| 24 | $(C_6H_5)_2P(t\text{-}C_4H_9)$ | 4.1 | 46 |
| 25 | $(C_6H_5)_3P$ | 16.0 | 55 |
| 26 | **$(C_6H_5)_3P$ | 10 | 54 |

*Gas chromatographic area percent of linear $C_8$—dialdehyde divided by the sum of the gas chromatographic areas of all the aldehyde products produced times 100.
**About 30 moles of $(C_6H_5)_3PO$ per mole of rhodium was also contained in the hydroformylation reaction medium.

The above data shows that the bisphosphine monooxide ligand of Example 22 gave a higher efficiency to straight chain $C_8$-dialdehyde product than either of the phosphorus ligands of Examples 23 to 26.

EXAMPLE 27

In a similar manner as described in Examples 1 to 10 propylene was hydroformylated using the following conditions.

About 15 ml. of a catalytic precursor solution containing about 250 ppm rhodium (introduced as rhodium dicarbonylacetylacetonate) and about 20 moles of $(C_6H_5)_2PCH_2CH_2P(O)(C_6H_5)_2$ bisphosphine monooxide ligand per mole of rhodium and dimethylformamide solvent was introduced into an autoclave as described in Examples 1 to 10. The precursor solution was maintained under nitrogen and heated to a hydroformylation reaction temperature of about 125° C. The hydroformylation reaction was conducted at a total gas pressure of about 80 psig. using 75 psia. of propylene, carbon monoxide and hydrogen in a 1:1:1 mole ratio. The initial hydroformylation reaction rate of aldehyde product observed upon a steady 5 psi. pressure drop was about 1.89 gram moles per liter per hour, while the hydroformylation reaction rate obtained after about 24 minutes of reaction time was about 1.74 gram moles per liter per hour which represents a decline in catalyst activity of only about 8 percent.

EXAMPLES 28 AND 29

Propylene was continuously hydroformylated into butyraldehyde in the following manner.

These long term catalyst stability experiments were conducted in a glass reactor operating in a continuous propylene hydroformylation mode. The reactor consisted of a three ounce pressure bottle submersed in an oil bath with a glass front for viewing. In each experiment about 20 ml. of a freshly prepared rhodium catalytic precursor solution was charged to the reactor with a syringe after purging the system with nitrogen. Each precursor solution contained about 200 ppm rhodium introduced as rhodium dicarbonyl acetylacetonate, a phosphorus ligand in the amount shown in TABLE VI below and Texanol ® (a mixture of butyraldehyde trimers) solvent. After closing the reactor, the system was again purged with nitrogen and the oil bath was heated to furnish the desired hydroformylation reaction temperature. The hydroformylation reaction in each experiment was conducted at a total gas pressure of about 165 psig. using about 100 psia. hydrogen, about 40 psia. propylene and about 10 psia. carbon monoxide, the remainder being nitrogen. The flows of the feed gases (carbon monoxide, hydrogen and propylene) were controlled individually with mass flow meters and the feed gases dispersed into the precursor solution via fritted glass spargers. The unreacted portion of the feed gases stripped out the product aldehydes and the outlet gas analyzed over two days of continuous operation at the reaction temperatures given in TABLE VI below. The average reaction rates for each experiment in terms of gram moles per liter per hour of product aldehydes for each day of operation are also given in TABLE VI below.

TABLE VI

| Example No. | Phosphorus Ligand | *P/Rh Ratio | Day | Temp. | Reaction Rate Gram Moles/Liter Hour |
|---|---|---|---|---|---|
| 28 | $(C_6H_3)_3P$ | 80 | 1 | 105° C. | 1.49 |
|  | " |  | 2 | 127° C. | 1.50 |
| 29. | $(C_6H_5)_2P(CH_2)_2\overset{O}{\overset{\|}{P}}(C_6H_5)_2$ | 20 | 1 | 105° C. | 0.70 |
|  | " |  | 2 | 127° C. | 1.40 |

*Mole Ratio of Phosphorus Ligand Per Mole of Rhodium.

The above data shows that the reaction rate of Example 29 (which employed a bisphosphine monooxide ligand) at 127° C. was twice as high as that obtained at 105° C. which is an indication of good high temperature catalyst stability. On the other hand the reaction rate of Example 28 (which employed triphenylphosphine ligand) at 127° C. did not improve over that obtained at 105° C. which indicates poor high temperature catalyst stability.

EXAMPLE 30

Propylene was continuously hydroformylated in a one gallon stainless steel autoclave employing a rhodium catalytic precursor solution containing about 260 ppm. rhodium introduced as rhodium dicarbonyl acetylacetonate, about 80 moles of monooxide of bisdiphenylphosphinoethane $[(C_6H_5)_2P(CH_2)_2P(O)(C_6H_5)_2]$ ligand and a solvent mixture of Texanol ® and 1,4-butanediol (3/1 volume ratio). A $CO/H_2$ gas ratio of about 10 psia. of carbon monoxide and 100 psia. of hydrogen was employed. The partial pressure of propylene employed is given in TABLE VII below. The continuous hydroformylation process was carried out over six days at about 130° C. and at about 140° C. for an additional three days. Gaseous aldehyde products were stripped from the reactor and condensed, the recovered unreacted feed gases being recycled to the reactor via a gas compressor. The product aldehydes were collected, weighed and analyzed and the results are given in TABLE VII below.

TABLE VII

| Day | Temp. °C. | Total Aldehyde Reaction Rate Gram Moles/ Liter Hour | ªN/I Butyraldehyde Ratio | Propylene Partial Pressure (psi) |
|---|---|---|---|---|
| 1 | 130 | 1.88 | 10.2 | 58.14 |
| 3 | 130 | 1.72 | 9.9 | 55.89 |
| 4 | 130 | 1.67 | 9.9 | 55.30 |
| 5 | 130 | 1.72 | 10.0 | 57.70 |
| 6 | 130 | 1.69 | 10.0 | 58.70 |
| 7 | 140 | 2.02 | 8.15 | 61.6 |
| 8 | 140 | 1.81 | 8.23 | 60.3 |
| 11 | 140 | 1.92 | 7.65 | 68.2 |

ªNumber of moles of normal butyraldehyde per mole of branched butyraldehyde product The above data shows that the reaction rate declined at an average rate of only about 1.7 percent per day over a period of six days at 130° C. demonstrating the high temperature stability of the bisphosphine monooxide ligand.

Various modifications and variations of this invention will be obvious to a worker skilled in the art and it is to be understood that such modifications and variations are to be included within the purview of this application and the spirit and scope of the appended claims.

What is claimed is:

1. A rhodium complex hydroformylation catalytic precursor composition consisting essentially of a solubilized rhodium carbonyl bisphosphine monooxide acetylacetonate complex, an organic solvent and free bisphosphine monooxide ligand; wherein the bisphosphine monooxide of said complex and said free bisphosphine monooxide ligand is an organic tertiary bisphosphine monooxide ligand having the general formula

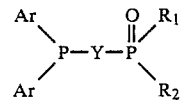

wherein each Ar group represents an identical or different substituted or unsubstituted aryl radical, each $R_1$ and $R_2$ group represents an identical or different substituted or unsubstituted monovalent hydrocarbon radical and Y represents a divalent bridging group.

2. A composition as defined in claim 1, wherein each Ar group represents an identical or different substituted or unsubstituted aryl radical containing from 6 to 12 carbon atoms; each $R_1$ and $R_2$ group represents an identical or different substituted or unsubstituted monovalent hydrocarbon radical containing from 1 to 30 carbon atoms and selected from the group consisting of alkyl, aryl, alkaryl, aralkyl and alicyclic radicals, and wherein Y represents a divalent bridging group containing from 1 to 30 carbon atoms selected from the group consisting of hydrocarbon radicals, oxygen containing hydrocarbon radicals, sulfur containing hydrocarbon radicals and nitrogen containing hydrocarbon radicals.

3. A composition as defined in claim 2, which contains from about 50 to about 400 ppm rhodium calculated as free metal having been introduced as rhodium dicarbonyl acetylacetonate, about 3 to about 80 moles of said free bisphosphine monooxide ligand per mole of rhodium present therein.

4. A composition as defined in claim 3, wherein $R_1$ and $R_2$ represent a substituted or unsubstituted monovalent hydrocarbon radical selected from the group consisting of alkyl radicals having from 1 to 12 carbon atoms and aryl radicals having from 6 to 12 carbon atoms, and wherein Y contains from 1 to 12 carbon atoms.

5. A composition as defined in claim 4, wherein each Ar radical is an unsubstituted aryl radical; $R_1$ and $R_2$ represent unsubstituted alkyl or aryl radicals, and Y is a divalent hydrocarbon radical.

6. A composition as defined in claim 5 wherein said organic tertiary bisphosphine monooxide ligand is a ligand having the formula

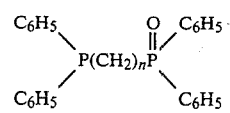

wherein n is an integer of 2 to 8.

7. A composition as defined in claim 6, wherein n is 2.

* * * * *